US010603269B2

(12) United States Patent
Argembeaux et al.

(10) Patent No.: US 10,603,269 B2
(45) Date of Patent: *Mar. 31, 2020

(54) COSMETIC PREPARATIONS WITH A FLOW POINT

(71) Applicant: Beiersdorf AG, Hamburg (DE)

(72) Inventors: Horst Argembeaux, Wentorf (DE); Andreas B. Kummer, Hamburg (DE); Katrin Counradi, Hamburg (DE); Thomas Raschke, Pinneberg (DE)

(73) Assignee: BEIERSDORF AG, Hamburg (DE)

( * ) Notice: Subject to any disclaimer, the term of this patent is extended or adjusted under 35 U.S.C. 154(b) by 193 days.

This patent is subject to a terminal disclaimer.

(21) Appl. No.: 14/650,709

(22) PCT Filed: Dec. 4, 2013

(86) PCT No.: PCT/EP2013/075495
§ 371 (c)(1),
(2) Date: Jun. 9, 2015

(87) PCT Pub. No.: WO2014/090651
PCT Pub. Date: Jun. 19, 2014

(65) Prior Publication Data
US 2015/0328135 A1    Nov. 19, 2015

(30) Foreign Application Priority Data
Dec. 12, 2012  (DE) .................. 10 2012 222 956

(51) Int. Cl.
| | | |
|---|---|---|
| *C11D 1/00* | (2006.01) | |
| *C11D 3/37* | (2006.01) | |
| *A61Q 19/10* | (2006.01) | |
| *A61K 8/90* | (2006.01) | |
| *A61K 8/20* | (2006.01) | |
| *A61Q 5/02* | (2006.01) | |
| *A61K 8/81* | (2006.01) | |
| *A61K 8/04* | (2006.01) | |
| *C08F 220/18* | (2006.01) | |
| *C08F 220/26* | (2006.01) | |

(52) U.S. Cl.
CPC ............ *A61K 8/90* (2013.01); *A61K 8/044* (2013.01); *A61K 8/20* (2013.01); *A61K 8/8152* (2013.01); *A61Q 5/02* (2013.01); *A61Q 19/10* (2013.01); *A61K 2800/262* (2013.01); *A61K 2800/48* (2013.01); *A61K 2800/54* (2013.01); *A61K 2800/548* (2013.01); *A61K 2800/592* (2013.01); *A61K 2800/594* (2013.01); *C08F 220/18* (2013.01); *C08F 220/26* (2013.01)

(58) Field of Classification Search
CPC .... A61K 8/0241; A61K 8/042; A61K 8/8152; A61K 2800/28; A61K 2800/262; C11D 1/00; C11D 3/37; C11D 3/3757; A61Q 19/10
See application file for complete search history.

(56) References Cited

U.S. PATENT DOCUMENTS

| | | | |
|---|---|---|---|
| 7,288,616 | B2 | 10/2007 | Tamareselvy et al. |
| 8,673,277 | B2 | 3/2014 | Tamareselvy et al. |
| 2003/0207988 | A1 | 11/2003 | Tamareselvy |
| 2007/0161524 | A1 | 7/2007 | Counradi et al. |
| 2008/0045646 | A1 | 2/2008 | Tamareselvy et al. |
| 2013/0115815 | A1 | 5/2013 | Tamareselvy et al. |
| 2013/0203866 | A1* | 8/2013 | Aleksandrovic-Bondzic ............. A61K 8/8152 514/772.6 |
| 2014/0336101 | A1 | 11/2014 | Mertens |

FOREIGN PATENT DOCUMENTS

| | | | | |
|---|---|---|---|---|
| DE | 19909803 | A1 | 9/2000 | |
| DE | 10344527 | A1 | 4/2005 | |
| DE | 102010022063 | | * 12/2011 | ............... C08F 2/22 |
| DE | 102010022063 | A1 | 12/2011 | |
| DE | 102011078087 | A1 | 12/2012 | |
| WO | WO 01/76552 | | * 10/2001 | ............... A61K 7/50 |
| WO | 2010121876 | A1 | 10/2010 | |
| WO | 2011151091 | A1 | 12/2011 | |
| WO | 2012006402 | A1 | 1/2012 | |
| WO | 2012168015 | A1 | 12/2012 | |
| WO | 2013017328 | A1 | 2/2013 | |

OTHER PUBLICATIONS

Database GNPD [Online] MINTEL; Jun. 1, 2013 (Jun. 1, 2013). "Queen of the Night Shower & Oil Pearls".
Clear Hydrating Body Wash with Suspended Beads, CL-B0004, Formulation Example of Messrs. Lubrizol, http://www.lubrizol.com/PersonalCare/CL-B0004-Clear-Hydrating-Body-Wash.pdf, Nov. 4, 2012.
Anonymous: "On Surfactants and Formulation (face wash, shampoo and shower gels)—It's all in my hands", Apr. 23, 2013, 11pgs, found on Internet: https://itsallinmyhands.com/2013/04/23/0n-surfactants-and-formulation-face-wash-shampoo-and-shower-gels/.

* cited by examiner

*Primary Examiner* — Brian P Mruk
(74) *Attorney, Agent, or Firm* — Abel Schillinger, LLP

(57) ABSTRACT

The invention relates to transparent preparations containing a cross-linked acrylate copolymer. Said preparations have a pH-value of between 4.0-7.0, in particular a pH-value of <6.4, suitable flowing properties and optionally suspended and stabilized particles.

6 Claims, No Drawings

COSMETIC PREPARATIONS WITH A FLOW POINT

BACKGROUND OF THE INVENTION

1. Field of the Invention

The present invention describes transparent, aqueous surfactant-containing preparations comprising one or more crosslinked acrylate copolymers. Such preparations may also have suspended or stabilized particles.

2. Discussion of Background Information

It has not been possible to date to provide transparent surfactant formulations with stabilized particles at a pH of 4.0 to 7.0, in particular a pH <6.4, which have suitable flow properties, are provided with a viscosity of ≥2000 mPa·s and have a high foaming ability. Known formulations also have a proportion of anionic surfactant of >10%. Due to the high proportion of anionic surfactants, they have a poor mildness. It is now in particular desirable to provide preparations which, in addition to transparency, the suitable flow properties which enable a stable suspension of particles, droplets and/or bubbles and a largely acidic pH, are cosmetically advantageous preparations which are characterized by suitable mildness and care properties.

Although systems using xanthan gum are already known from the prior art, these have cosmetic properties which can be improved with respect to skin feel during and after application. Moreover, only lower viscosities are reached at the same use concentration.

SUMMARY OF THE INVENTION

To achieve advances in the field of stabilizing gel-like systems at the same time as improving the application properties, experiments were undertaken in which xanthan gum was replaced by polymeric structures. Crosslinked acrylate-based polymers proved to be particularly suitable. By using these polymeric structures, preparations could be provided which form a yield point. It is thereby possible to stabilize solid particles, droplets and bubbles in aqueous systems. These preparations thus obtained usually have a pH of ≥5.5. In preparations from the prior art which also lead to transparent preparations with yield point below a pH of 5.5, turbidity occurs on prolonged storage and the cosmetic consistency is unfavorable and in need of improvement.

In the preparation of acrylate-based polymers, the choice of monomers, the ratio of the monomers to one another and the course of the polymerization reaction play an important role. The reaction course in particular influences the properties of the resulting products. The polymerization reaction can be carried out as follows: Firstly, monomers are treated with an initiator (ammonium peroxodisulfate for example) to start the reaction. After 30 minutes, crosslinker molecules are added and a further addition of monomer takes place. The reaction then proceeds for 4 hours. Variations in the reaction times are possible. The resulting products have a homogeneous composition. The monomers used are, for example:

acidic vinyl monomers and/or salts thereof,
  nonionic vinyl monomers, preferably hydrophobic nonionic monomers,
  monomers comprising an unsaturated end group and a polyoxyalkylene moiety, and
  crosslinking monomers.

The preparation of homogeneous crosslinked acrylate-based copolymers is described below by way of example. These polymers are obtainable by free-radical emulsion polymerization of (A) at least one acidic vinyl monomer or salt thereof, (B) at least one nonionic vinyl monomer, particularly preferably a hydrophobic nonionic vinyl monomer, (C) at least one monomer comprising an unsaturated end group and a polyoxyalkylene moiety, (D) at least one crosslinking monomer, (E) optionally a protective colloid, characterized in that the polymerization is controlled such that (F) the gel effect occurs at least temporarily, achieved in that the monomer addition of the monomers (A), (B) and (C) (metering period) takes place over 120 minutes, preferably 60 minutes, particularly preferably 40 minutes, especially preferably 30 minutes and (G) the addition of the crosslinking monomer (D) begins at the earliest 10 minutes, preferably at the earliest 15 minutes after the first addition of the monomers (A), (B) and (C). In such a polymerization utilizing the Trommsdorff effect, i.e. at constant addition of the monomers and at the same time high addition rate of the monomers, a monomer excess forms which leads to autoacceleration of the polymerization (Trommsdorff effect). The result is an increase in the molecular weights at the same time as advantageous morphology of the polymers. It is advantageous here if the temperature during the polymerization is maintained between 70 and 90° C., preferably 80 and 90° C. It is further advantageous if the addition of initiator takes place both before starting the metering period and after addition of the crosslinking monomer. It is particularly preferable in this case if (H) associative monomers are absent or at most have a concentration of 15% by weight, preferably 10% by weight, particularly preferably 5% by weight, very particularly preferably 2.5% by weight, exceptionally preferably 1% by weight, particularly exceptionally preferably 0.1% by weight. It is particularly preferable if the acidic vinyl monomer (A) is selected from vinyl monomers having carboxyl groups, particularly preferably acrylic acid or methacrylic acid or alkali metal, alkaline earth metal, ammonium or alkylammonium salts thereof. It is particularly preferable if the nonionic vinyl monomer (B) is selected from the group of C1-C22 alkyl acrylates and the C1-C22 alkyl methacrylates and also mixtures thereof. Good flow properties and thus an advantageous rheological profile are thereby achieved. It is particularly preferable if the monomer (C), comprising an unsaturated end group and a polyoxyalkylene moiety, is selected from vinylpolyalkylene glycols or polymerizable surfactants or mixtures thereof, is particularly preferably selected from vinylpolyalkylene glycols or polymerizable surfactants or mixtures thereof, is preferably selected from ethoxylated and propoxylated 1,4-butanediol vinyl ether having 30 ethyleneoxy and propyleneoxy units, allylpolyethylene glycol ether having 30 ethyleneoxy units, allylpolyethylene glycol ether having 20 ethyleneoxy units, vinylpolyethylene glycol ether having 20 ethyleneoxy units, CH2=CHCH2O[(CH2CH2O)n(CH2(CH3)CHO)]mCH3 where m+n=5 to 100 and n/m=1, polyalkylene glycol allyl butyl ether having 25 ethyleneoxy and 8 propyleneoxy units, very particular preference being given to using Emulsogen R307 (EO/PO 30 1,4-butanediol vinyl ether (EO/PO 30 mol), Clariant), Emulsogen RAL307 (allylpolyalkylene glycol ether (EO 30 mol), Clariant), Polyglycol A11/1800 (allylpolyalkylene glycol ether (EO 20 mol, PO 20 mol), Clariant), Polyglycol R1100 (vinylpolyalkylene glycol ether (EO 20 mol), Clariant), Pluriol A111R (allyl alcohol alkoxylate, BASF) or Polyglycol AB25-8 (polyalkylene glycol allyl butyl ether (EO 25 mol, PO 8 mol), Clariant). Polyglycol A11/1800 has proven to be particularly useful and is therefore exceptionally preferred. It is particularly preferred if the crosslinking monomer (D) is selected from polyol(meth)acrylates with at least two (meth)acrylate groups and the mixed esters of polyols with acrylic acid and/or methacrylic acid. It is further particularly preferred if the monomers (A) are present at contents of 10 to 75%, preferably 20 to 60%, particularly preferably 28 to 52%, very particularly preferably 32 to 52%, (B) are present at contents of 10 to 90%, preferably 30 to 80%, particularly preferably 40 to 62%, very particularly preferably 40 to 60%, (C) are present at contents of 0.5 to 40%, preferably 1 to 10%, particularly preferably 2 to 6%, (D) are present at contents of up to 1%, preferably 0.05 to 0.5%, particularly preferably 0.1 to 0.3%. It is very particularly preferred if the monomers (A):(B) are present in mass ratios of 1:2.2 to 1.5:1, preferably 1:1.6 to 1.3:1. It is very particularly preferred if the addition of the crosslinking monomer starts at the earliest after 10 minutes, particularly preferably after 15 minutes, and either ends immediately or lasts until the end of the metering period of the monomers.

The products formed by such reactions may be referred to as homogeneous, crosslinked, acrylate-based copolymers. Such reactions and products are described, for example, in DE 102011078087. Homogeneous, crosslinked, acrylate-based copolymers, which are obtained with the preparation method described in DE 102011078087, are referred to as AMA-X polymers hereinafter.

The teaching for preparing the AMA-X polymers listed above was disclosed in DE 102011078087. DE 102011078087 is hereby incorporated in its entirety in the disclosure of this application.

For a person skilled in the art, it has now been found, surprisingly, that aqueous, surfactant-containing preparations comprising one or more AMA-X polymers redress the disadvantages of the prior art.

It is preferred, in accordance with the invention, if the concentration of at least one AMA-X polymer is 0.1 to 5.0%, preferably 0.5 to 4.0%, particularly preferably 1.0 to 2.0%, based on the active content and the total weight of the preparation.

It is also in accordance with the invention if the aqueous, surfactant-containing preparations according to the invention comprise particles, droplets and/or bubbles which are largely stably suspended and also remain largely stably suspended.

It is likewise in accordance with the invention if the aqueous, surfactant-containing preparations according to the invention are transparent preparations with or without particles, droplets and/or bubbles, where transparent preparations are characterized by turbidity values <30 NTU, preferably <25 NTU, particularly preferably ≤20 NTU.

It is also in accordance with the invention that the preparations described above have a pH of 4.0 to 7.0, preferably 4.0 to <6.4, particularly preferably 4.0 to ≤5.5.

It is particularly preferred in accordance with the invention if the preparations according to the invention have a pH of 4.0 to 7.0, preferably 4.0 to <6.4, particularly preferably 4.0 to ≤5.5 and are transparent preparations characterized by turbidity values <30 NTU, preferably <25 NTU, particularly preferably ≤20 NTU.

It is also preferred in accordance with the invention that the preparations according to the invention have a viscosity ≥2000 mPa·s.

It is also in accordance with the invention that the tan delta values for the preparations described above are 0.05 to 0.6, preferably 0.1 to 0.5.

It is also preferred in accordance with the invention that the preparations described above have a yield point of 0.5 to 20 Pa, preferably 1 to 6 Pa. It is furthermore in accordance with the invention that particles, droplets and/or bubbles are virtually homogeneously distributed and also remain in the preparation. The particles or droplets have a diameter of 0.1 to 2000 μm, furthermore a density of 0.001 to 2 g/cm$^3$.

It is also preferred in accordance with the invention that the preparations according to the invention, in particular transparent cleansing preparations, are free from xanthan gum. It is furthermore in accordance with the invention that the preparations have a viscosity ≥2000 mPa·s and are free from xanthan gum.

It is also preferred in accordance with the invention if further structure-forming polymers are present in addition to AMA-X polymers. It is furthermore in accordance with the invention if the concentration of AMA-X polymers and further structure-forming polymers is 0.1 to 5.0% by weight, preferably 0.2 to 4.0% by weight, particularly preferably 0.5 to 2.0% by weight, based on the active content in the preparations.

It is also in accordance with the invention that the preparations comprise 1.0 to 15% by weight of anionic surfactants, preferably 1.0 to <12% by weight.

It is furthermore in accordance with the invention that anionic surfactants are used in combination with 1.0 to 20% by weight of amphoteric, nonionic and/or cationic surfactants.

It is furthermore in accordance with the invention that the preparations according to the invention comprise skincare and/or haircare substances, preference being given to using glycerol, vegetable oils, paraffin oils or panthenol, silicones, cationic polymers, emollients, individually or in combination. The skincare and/or haircare substances are present at a content of 0.01 to 10% by weight, preferably 0.1 to 8% by weight, particularly preferably 0.2 to 5% by weight.

It is in accordance with the invention if the preparations according to the invention comprise salts, wherein preference is given to alkali metal salts, particularly alkali metal halides, alkali metal sulfates, alkali metal nitrates and/or alkali metal phosphates. The salt(s) is/are used in concentrations of 0.1 to 3.0% by weight.

In accordance with the invention, particular preference is given to preparations according to the invention comprising anionic surfactants at a content of 1.0 to 15% by weight, preferably 1.0 to <12% by weight and skincare substances, preferably glycerol, vegetable oils, paraffin oils or panthenol, individually or in combination.

It is preferred in accordance with the invention if the preparations according to the invention comprise substances which are specifically suitable for application to hair and scalp, for example, substances for care and conditioning of hair, and also substances having specific effects such as antidandruff active ingredients.

The invention also includes shower gels, facial cleansers, shampoos or cosmetic hydrogels comprising one or more AMA-X polymers.

The invention also includes the use of the preparations described above for cosmetic application.

The invention also includes the use of the preparations described above for cleansing the skin, particularly human skin.

The invention also includes the use of the preparations described above for application to hair, particularly for cleansing hair, particularly preferably for cleansing human hair.

The invention also includes the use of AMA-X polymers in aqueous, surfactant-containing preparations, in which tan delta values of 0.05 to 0.6, preferably 0.1 to 0.5 are determined.

The invention also includes a method for reducing skin irritation during the cleansing process, wherein the cleansing preparations
- are transparent, characterized by turbidity values below 30 NTU, preferably below 25 NTU, particularly preferably are below or equal to 20 NTU,
- comprise one or more crosslinked acrylate copolymers, particularly AMA-X polymers, at a content of 0.1 to 5.0%, preferably 0.5 to 4.0%, particularly preferably 1.0 to 2.0%, based on the active content and the total weight of the preparation,
- optionally comprise particles, droplets and/or bubbles virtually homogeneously distributed in the preparations,
- optionally comprise further structure-forming polymers, at a content of AMA-X polymers and structure-forming polymers of 0.1 to 5.0%, preferably 0.2 to 4.0%, particularly preferably 0.5 to 2.0%, based on the active content,
- optionally comprise 0.1 to 3.0% by weight of an inorganic salt selected from the group of the alkali metal halides, the alkali metal sulfates, the alkali metal nitrates and the alkali metal phosphates,
- have a pH of 4.0 to 7.0, preferably 4.0 to <6.4, particularly preferably 4.0 to ≤5.5 and
- a viscosity of ≥2000 mPa·s,
- comprise anionic surfactants at a content of 1.0 to 15% by weight, preferably <12% by weight and
- optionally comprise haircare substances at a content of 0.01 to 10% by weight.

The invention also includes a method for cleansing sensitive, delicate and dry skin, wherein the cleansing preparations
- are transparent, characterized by turbidity values below 30 NTU, preferably below 25 NTU, particularly preferably are below or equal to 20 NTU,
- comprise one or more crosslinked acrylate copolymers, particularly AMA-X polymers, at a content of 0.1 to 5.0%, preferably 0.5 to 4.0%, particularly preferably 1.0 to 2.0%, based on the active content and the total weight of the preparation,
- optionally comprise particles, droplets and/or bubbles virtually homogeneously distributed in the preparations,
- optionally comprise further structure-forming polymers, at a content of AMA-X polymers and structure-forming polymers of 0.1 to 5.0%, preferably 0.2 to 4.0%, particularly preferably 0.5 to 2.0%, based on the active content,
- optionally comprise 0.1 to 3.0% by weight of an inorganic salt selected from the group of the alkali metal halides, the alkali metal sulfates, the alkali metal nitrates and the alkali metal phosphates,
- have a pH of 4.0 to 7.0, preferably 4.0 to <6.4, particularly preferably 4.0 to ≤5.5 and
- a viscosity of ≥2000 mPa·s,
- comprise anionic surfactants at a content of 1.0 to 15% by weight, preferably <12% by weight and
- optionally comprise haircare substances at a content of 0.01 to 10% by weight.

The invention also includes a method for reducing the drying out of hair and/or the resulting brittle hair, wherein cleansing preparations
- are transparent, characterized by turbidity values below 30 NTU, preferably below 25 NTU, particularly preferably are below or equal to 20 NTU,
- comprise one or more crosslinked acrylate copolymers, particularly AMA-X polymers, at a content of 0.1 to 5.0%, preferably 0.5 to 4.0%, particularly preferably 1.0 to 2.0%, based on the active content and the total weight of the preparation,
- optionally comprise particles, droplets and/or bubbles virtually homogeneously distributed in the preparations,
- optionally comprise further structure-forming polymers, at a content of AMA-X polymers and structure-forming polymers of 0.1 to 5.0%, preferably 0.2 to 4.0%, particularly preferably 0.5 to 2.0%, based on the active content,
- optionally comprise 0.1 to 3.0% by weight of an inorganic salt selected from the group of the alkali metal halides, the alkali metal sulfates, the alkali metal nitrates and the alkali metal phosphates,
- have a pH of 4.0 to 7.0, preferably 4.0 to <6.4, particularly preferably 4.0 to ≤5.5 and
- a viscosity of ≥2000 mPa·s,
- comprise anionic surfactants at a content of 1.0 to 15% by weight, preferably <12% by weight and
- optionally comprise skincare and/or haircare substances at a content of 0.01 to 10% by weight.

The invention also encompasses a method for care of skin and/or hair during the cleansing process, wherein cleansing preparations
- are transparent, characterized by turbidity values below 30 NTU, preferably below 25 NTU, particularly preferably are below or equal to 20 NTU,
- comprise one or more crosslinked acrylate copolymers, particularly AMA-X polymers, at a content of 0.1 to 5.0%, preferably 0.5 to 4.0%, particularly preferably 1.0 to 2.0%, based on the active content and the total weight of the preparation,
- optionally comprise particles, droplets and/or bubbles virtually homogeneously distributed in the preparations,
- optionally comprise further structure-forming polymers, at a content of AMA-X polymers and structure-forming polymers of 0.1 to 5.0%, preferably 0.2 to 4.0%, particularly preferably 0.5 to 2.0%, based on the active content,
- optionally comprise 0.1 to 3.0% by weight of an inorganic salt selected from the group of the alkali metal halides, the alkali metal sulfates, the alkali metal nitrates and the alkali metal phosphates,
- have a pH of 4.0 to 7.0, preferably 4.0 to <6.4, particularly preferably 4.0 to ≤5.5 and
- a viscosity of ≥2000 mPa·s,
- comprise anionic surfactants at a content of 1.0 to 15% by weight, preferably <12% by weight and
- comprise skincare and/or haircare substances at a content of 0.01 to 10% by weight.

The invention likewise encompasses methods for reducing skin irritation during the cleansing process, for cleansing sensitive, delicate and dry skin and/or reducing the drying out of hair and/or the resulting brittle hair, wherein the cleansing preparations are transparent, characterized by turbidity values below 30 NTU, preferably below 25 NTU, particularly preferably are below or equal to 20 NTU, comprise one or more crosslinked acrylate copolymers, particularly AMA-X polymers, at a content of 0.1 to 5.0%, preferably 0.5 to 4.0%, particularly preferably 1.0 to 2.0%, based on the active content and the total weight of the preparation, optionally comprise particles, droplets and/or bubbles virtually homogeneously distributed in the preparations, optionally comprise further structure-forming polymers, at a content of AMA-X polymers and structure-forming polymers of 0.1 to 5.0%, preferably 0.2 to 4.0%, particularly preferably 0.5 to 2.0%, based on the active content, optionally comprise 0.1 to 3.0% by weight of an inorganic salt selected from the group of the alkali metal halides, the alkali metal sulfates, the alkali metal nitrates and the alkali metal phosphates, have a pH of 4.0 to 7.0, preferably 4.0 to <6.4, particularly preferably 4.0 to ≤5.5 and a viscosity of ≥2000 mPa·s, comprise anionic surfactants at a content of 1.0 to 15% by weight, preferably <12% by weight and optionally comprise skincare and/or haircare substances at a content of 0.01 to 10% by weight and have a mildness, measured as the L/D quotient in the RBC assay, with values of ≤0.4, preferably ≤0.35.

The viscosity values, which are disclosed in the present specification, have been measured at 25° C. using the Rheomat R123 from the company ProRheo. When measuring using the Rheomat R123, the rotor of the device is immersed bubble-free into the sample up to the mark. For the measurements, measuring bob 1 was used. Further information regarding the Rheomat R123 is published on the internet, see http://www.prorheo.de/fileadmin/user_upload/pdfs/R123.pdf and http://www.prorheo.de/fileadmin/user_upload/pdfs/Bedienung_R123_d.pdf.

The formulations have a tan delta of ≤0.5, by which a stabilization of particles is given. Tan delta is understood to mean the quotient of the loss modulus and the storage modulus. The tan delta is determined as follows:

Loss and storage moduli are measured by a dynamic, shear-stress-controlled frequency test at a shear stress of 1 Pa on a shear-stress-controlled rheometer (SR series from Rheometric Scientific or AR series from TA instruments or other) at 40° C.±1° C. with 25 mm parallel plate geometry at a gap between 0.8 mm and 1.2 mm, charging being carried out in a structure-preserving manner. The frequency test is carried out according to the prior art with an appropriate structure recovery time before the test and the tan delta is quoted in the frequency range between 0.05 rad/s and 3.0 rad/s, preferably between 0.08 rad/s and 1.0 rad/s.

The yield point is considered to be the critical shear stress of the flow curve. It may be determined in accordance with the invention as follows:

The flow curve is measured on a shear-stress-controlled rheometer at 25° C.±1° C. with 20 mm parallel plate geometry at a gap between 0.8 mm and 1.2 mm, with charging being carried out in a structure-preserving manner A suitable constant shear stress gradient is predefined and, before the test, a corresponding structure recovery time is observed and the critical shear stress at the maximum of the flow curve is given.

To determine the mildness, an RBC assay is carried out.

The standard RBC assay (10 minutes incubation) serves to estimate the in vivo mucous membrane of the eye irritation potential of surfactants and surfactant-containing products.

1. Hemolysis

A defined aliquot of isolated calf erythrocytes is incubated for 10 minutes with shaking at room temperature (RT) with a series of increasing concentrations of the WAS test samples to be investigated (stock solution with formulations 1:100 w/v or 0.1% active content in PBS for raw materials). After centrifugation, the resulting supernatants are analyzed photometrically at 530 nm for their liberated hemoglobin ($HbO_2$) content. The relative degree of hemolysis is thereby calculated and the parameter H50 [μl/ml] is determined from the concentration-response curve. This indicates the concentration of the test samples at which 50% of hemoglobin is liberated.

2. $HbO_2$ Denaturation

A defined aliquot of isolated calf erythrocytes is incubated for 10 minutes with shaking at RT with a fixed concentration of test sample (1% w/v or 0.1% active content) and then centrifuged. The change in spectral absorption at 575 nm and 540 nm is measured compared to native $HbO_2$. The denauration index DI [%] is calculated from the ratio of the absorption values to each other. Na lauryl sulfate serves as 100% standard (0.1% active content).

3. L/D Quotient

The quotient is the ratio of the hemolysis parameters (H50) and denaturation (DI) and is used to characterize and classify the test samples investigated.

Turbidity values are measured using a turbidity measuring device, wherein distilled water is used as standard with a value of NTU=0.

Further Structure-Forming Polymers:

Further polymers can optionally be used for thickening and stabilizing particles, which may be selected from the group of polysaccharides or derivatives thereof, e.g. hyaluronic acid, hydroxypropyl methylcellulose, particularly advantageously from the group of the polyacrylates, preferably a polyacrylate from the group of so-called carbopols, for example, carbopols of the types 980, 981, 1382, 2984, 5984, Ultrez 2020, Ultrez 10 or Pemulen TR1 or also ethoxylated glycerol fatty acid esters and derivatives thereof such as hydrogenated glyceryl palmate, PEG-90 glyceryl isostearate, in each case individually or in combination.

Surfactants:

The surfactants used in the preparations according to the invention may be anionic surfactants in combination with amphoteric, nonionic and/or cationic surfactants.

Anionic surfactants which could be advantageously used are:

acylamino acids (and salts thereof), such as
1. Acyl glutamates, for example, sodium acyl glutamate, sodium cocoyl glutamate, di-TEA-palmitoyl aspartate and sodium caprylic/capric glutamate,
2. Acyl peptides, for example, palmitoyl hydrolyzed milk protein, sodium cocoyl hydrolyzed soy protein and sodium/potassium cocoyl hydrolyzed collagen,
3. Sarcosinates, for example, myristoyl sarcosine, TEA lauroyl sarcosinate, sodium lauroyl sarcosinate and sodium cocoyl sarcosinate,
4. Taurates, for example, sodium lauroyl taurate and sodium methyl cocoyl taurate, 5. Acyl lactylates, lauroyl lactylate, caproyl lactylate,
6. Alaninates, carboxylic acids and derivatives such as
1. Carboxylic acids, for example, lauric acid, aluminum stearate, magnesium alkanolate and zinc undecylenate, stearic acid/salt, palmitic acid/salt,
2. Ester carboxylic acid, for example, calcium stearoyl lactylate, laureth-6 citrate and sodium PEG-4 lauramide carboxylate,
3. Ether carboxylic acids, for example, sodium laureth-13 carboxylate and sodium PEG-6 cocamide carboxylate, phosphoric esters and salts, such as DEA Oleth-10 phosphate and dilaureth phosphate, sulfonic acids and salts, such as
1. Acyl isethionates, e.g sodium/ammonium cocoyl isethionate, sodium lauroyl methyl isethionate,
2. Alkyl aryl sulfonates,
3. Alkyl sulfonates, for example, sodium coco monoglyceride sulfate, sodium C12-14 olefin sulfonate, sodium lauryl sulfoacetate and magnesium PEG-3 cocamide sulfate,
4. Sulfosuccinates, for example, dioctyl sodium sulfosuccinate, disodium laureth sulfosuccinate, disodium lauryl sulfosuccinate, disodium undecyleneamido-MEA sulfosuccinate and PEG-5 lauryl citrate sulfosuccinate, and also
sulfuric acid esters, such as
1. Alkyl ether sulfate with various degrees of ethoxylation and mixtures thereof, for example, sodium, ammonium, magnesium, MIPA or TIPA laureth-X sulfate, sodium myreth-X sulfate and sodium C12-13-pareth-X sulfate, where X=1-5 ethoxy groups,
2. Alkyl sulfates, for example, sodium, ammonium and TEA lauryl sulfate, sodium, ammonium and TEA coco sulfate.

Cationic surfactants which could be advantageously used are:
1. Alkylamines,
2. Alkylimidazoles,
3. Ethoxylated amines,
4. Quaternary surfactants, for example, cetyl trimethylammonium halide,
5. Ester quats, for example, dicocoylethyl hydroxyethylmoium methosulfates and
6. Amide quats, for example, palmitamidopropyltrimonium chloride.

Quaternary surfactants comprise at least one N atom, which is covalently bonded to 4 alkyl and/or aryl groups. This leads to a positive charge irrespectively of the pH. Advantageous quaternary surfactants are alkyl betaine, alkylamidopropyl betaine and alkylamidopropyl hydroxysulfaine. Cationic surfactants in the context of the present invention may further preferably be selected from the group of quaternary ammonium compounds, in particular benzyltrialkylammonium chlorides or bromides, such as benzyldimethylstearylammonium chloride, furthermore alkyltrialkylammonium salts, for example, cetyltrimethylammonium chloride or bromide, alkyldimethylhydroxyethylammonium chloride or bromide, dialkyldimethylammonium chloride or bromide, alkylamide ethyltrimethylammonium ether sulfates, alkylpyridinium salts, for example, lauryl or cetyl pyrimidinium chloride, imidazoline derivatives and compounds having cationic character, such as amine oxides, for example, alkyldimethylamine oxides or alkylaminoethyl dimethylamine oxides. The use of cetyltrimethylammonium salts is particularly advantageous.

Amphoteric surfactants which could be advantageously used are
1. Acyl/dialkyl ethylenediamine, for example, sodium acyl amphoacetate, disodium acyl amphodipropionate, disodium alkyl amphodiacetate, disodium cocoamphodiacetate, disodium cocoamphomonoacetate, sodium acyl amphohydroxypropyl sulfonate, disodium acyl amphodiacetate, and sodium acyl amphopropionate,
2. N-alkylamino acids, for example, aminopropyl alkylglutamide, alkylaminopropionic acid, sodium alkylimidodipropionate and lauroamphocarboxyglycinate,
3. Betaines, for example, coco betaine, cocoamidopropyl betaine,
4. Sultaines, for example, lauryl hydroxysultaine.

Nonionic surfactants which could be advantageously used are
1. Alcohols,
2. Alkanolamides, such as cocamide MEA/DEA/MIPA,
3. Amine oxides, such as cocoamidopropylamine oxide,
4. Esters, which are formed by esterification of carboxylic acids with ethylene oxide, glycerol, sorbitan or other alcohols,
5. Ethers, for example, ethoxylated/propoxylated alcohols, laureth-X where X=2 to 10, wherein X signifies ethoxy groups, ethoxylated/propoxylated esters, ethoxylated/propoxylated glycerol esters, PEG-200 hydrogenated glyceryl palmate, ethoxylated/propoxylated cholesterols, ethoxylated/propoxylated triglyceride esters, ethoxylated propoxylated lanolin, ethoxylated/propoxylated polysiloxanes, propoxylated POE ethers and alkylpolyglycosides such as lauryl glucoside, decyl glycoside and coco glycoside,
6. Sucrose esters, sucrose ethers,
7. Polyglycerol esters, diglycerol esters, monoglycerol esters,
8. Methylglucose esters, esters of hydroxyacids.

UV Filter:

In the context of the present invention it is advantageous to add sun protection filters to the preparations. The main purpose of these preparations, however, is not protection from sunlight but they nevertheless comprise a content of UV protecting substances.

It is advantageous in the context of the present invention if the UV filter substances used are water-soluble.

Water-soluble UV filter substances in accordance with the invention are, for example:

Salts of 2-phenylbenzimidazole-5-sulfonic acid, such as sodium, potassium or triethanolammonium salts thereof, and also the sulfonic acid itself;

Sulfonic acid derivatives of 3-benzylidene camphor, such as 4-(2-oxo-3-bornylidenemethyl)benzenesulfonic acid, 2-methyl-5-(2-oxo-3-bornylidenemethyl)sulfonic acid and salts thereof.

Oil-soluble UV filters linked to polymers can also, such as polysilicone-15, which can also be obtained under the trade name Parsol SLX.

In the context of the present invention, preference is given to using benzophenone-4 for example.

The total amount of filter substances is selected in the range of 0.01 to 30% by weight, preferably 0.02 to 10% by weight, in each case based on the total weight of the preparations.

Solvent:

The preparations according to the invention may optionally advantageously comprise alcohols, diols or polyols having a low carbon number, and also ethers thereof, preferably ethanol, isopropanol, 1,2-propanediol, propylene glycol, ethylene glycol, ethylene glycol monoethyl or monobutyl ether, propylene glycol monomethyl, monoethyl or monobutyl ether, diethylene glycol monomethyl or monoethyl ether and analogous products.

Preservatives:

To preserve the present preparations, the preservatives commonly used in cosmetics may be used. These include, for example, parabens such as methylparaben, propylparaben, ethylparaben and butylparaben. Other preserving substances can also be used, such as methylisothiazolinone and hydantoins such as DMDM hydantoins. It is also desirable, however, to use preservatives based on acid, which are used in the food industry. Included here are, for example, benzoic acid and/or salicylic acid and/or salts thereof. Since these preservatives exert their effect in an acidic pH range, a pH range which is advantageous for human skin (pH of human skin 5.4 to 5.9, in some areas of the skin even below pH=5.0) and is unfavorable for many bacteria, the use of these preservatives is of great advantage.

Skincare Substances:

It is advantageous to add substances to the preparations according to the invention which support skincare, which protect against dehydration of the skin, reduce irritation, which make the skin smoother and softer and improve the appearance of the skin. These include glycerol, panthenol, fatty acids having a chain length of C8 to C22, fatty alcohols having a chain length of C14 to C22, paraffin oils and also vegetable oils.

Haircare Substances:

In addition to the skincare substances described which also provide a degree of care to hair, which is reflected, inter alia, in improved stylability and a pleasant feel, silicones, cationic polymers and further haircare substances can also be added to the preparations according to the invention.

pH Adjustment:

The adjustment of the pH can be effected in the usual way in the cosmetic industry. However, preference is given to using citric acid and sodium hydroxide in order to adjust the required pH.

Salts:

The preparations according to the invention may also advantageously comprise salts. These salts are preferably inorganic salts. Alkali metal salts such as alkali metal halides, alkali metal sulfates, alkali metal nitrates and alkali metal phosphates are particularly advantageous.

Complexing Agents:

It is also optionally advantageous in accordance with the invention to add complexing agents to the preparations. Complexing agents are auxiliaries known per se in cosmetology or medical galenics. By complexing disrupting metals such as Mn, Fe, Cu and others, it is possible, for example, to prevent undesired chemical reactions in cosmetic or dermatological preparations.

Complexing agents, particularly chelators, form complexes with metal atoms which, in the presence of one or more polybasic complexing agents, i.e. chelators, are metallacycles. Chelates are compounds in which a single ligand occupies more than one coordination site on a central atom. In this case, normally extended compounds are thus closed as a result of complex formation via a metal atom or a metal ion to form rings. The number of bonded ligands depends on the coordination number of the central metal. A prerequisite for formation of the chelate is that the compound reacting with the metal comprises two or more atomic groupings which act as electron donors.

The complexing agent(s) can advantageously be selected from the group of customary compounds, preferably at least one substance from the group consisting of tartaric acid and anions thereof, citric acid and anions thereof, aminopolycarboxylic acids and anions thereof (such as ethylenediaminetetraacetic acid (EDTA) and anions thereof, nitrilotriacetic acid (NTA) and anions thereof, hydroxyethylenediaminotriacetic acid (HOEDTA) and anions thereof, diethyleneaminopentaacetic acid (DPTA) and anions thereof, trans-1,2-diaminocyclohexanetetraacetic acid (CDTA) and anions thereof) and tetrasodium iminodisuccinate.

According to the invention, the complexing agent(s) is/are advantageously present in cosmetic or dermatological preparations preferably in amounts of 0.01% by weight to 10% by weight, preferably 0.05% by weight to 5% by weight, particularly preferably 0.1-2.0% by weight, based on the total weight of the preparations.

Particles:

In the context of the present specification, particles are particles of all organic and inorganic solids on a natural and synthetic basis. Use is made, for example, of plastic particles of, for example, viscose, cellulose, polypropylene, polyester, polyethylene terephthalate (PET), polytetrafluoroethylene (PTFE), aramid, nylon, kevlar, polyurethanes, polystyrene, cellulose esters and/or polyethylene and all other types of ground stone, ground plant constituents such as nut shells and kernels. Mixtures of different particles are also contemplated, which are pelleted by suitable physical processes, such as compression. Preference is given, for example, to Unispheres® from Induchem or Cosmospheres® from Pelletech.

It is naturally known to the person skilled in the art that cosmetic preparations are in most cases inconceivable without the customary auxiliaries and additives. The cosmetic preparations according to the invention can accordingly also comprise cosmetic auxiliaries, as are customarily used in such preparations, for example, perfumes, substances for preventing foaming, dyes, pigments which have a coloring effect, emulsifiers, softening, antiinflammatory substances, insect repellants, antidandruff active ingredients, bactericides, viricides, salts, antimicrobially, proteolytically or keratolytically effective substances or other customary constituents of a cosmetic formulation such as foam stabilizers and electrolytes.

By using AMA-X polymers, transparent formulations could be developed in a pH range of 4.0 to 7.0, preferably 4.0 to <6.4, particularly preferably 4.0 to ≤5.5. Transparent formulation signifies that the turbidity values are below 30 NTU, preferably below 25 NTU, particularly preferably below or equal to 20 NTU. These formulations have suitable flow properties, characterized by tan delta values which are preferably ≤0.5, such that solid particles, droplets and/or bubbles are stably suspended and also remain so.

Since the content of anionic surfactants in the preparations according to the invention is below 10% and a combination of anionic surfactants with amphoteric, nonionic and/or cationic surfactants can be used, these preparations are characterized by their mildness. These formulations prepared in such a way have turbidity values <30 NTU, preferably <25 NTU, particularly preferably ≤20 NTU and a preferred tan delta ≤0.5. The use of haircare substances increases the mildness of these preparations still further. This is made clear by a comparative test (see examples, comparative test to determine mildness), in which a commercial product was compared with a preparation according to the invention with respect to mildness. The commercial product used is Balea Dusche & Ölperlen Queen of the Night, which preparation comprises Aqua SF2 from Lubrizol as structure-giving polymer. The preparation according to the invention achieves better values than the commercial product with respect to mildness, measured with the standard RBC test (WAS). The results are listed under examples in the comparative test to determine mildness. Since the preparations according to the invention are identified as mild preparations, said preparations are particularly suitable for achieving a reduction in irritation of the skin during the cleansing process, for cleansing sensitive, delicate and dry skin and for achieving a reduction of the drying out of hair and/or to be effective against the resulting brittle hair.

Moreover, the preparations according to the invention are extremely satisfactory products with respect to the appearance of the products. No "polymer clouds" are visible such as in products which comprise Aqua SF2 (from Lubrizol) as structure-giving polymer, which can be observed under certain conditions. Likewise, no polymer precipitates can be seen in the preparations according to the invention. These polymer precipitates, which can be observed in products comprising Aqua SF2, lead to adhesion of product and/or polymer to the walls of the packaging. The preparations according to the invention are uniformly transparent preparations with exceptionally satisfactory flow behavior.

DETAILED DESCRIPTION OF THE INVENTION

The examples which follow illustrate the invention without limiting it.

EXAMPLES

| Shower gels (the quantities are active contents) | | | | | | | |
|---|---|---|---|---|---|---|---|
| Example No. | 1 | 2 | 3 | 4 | 5 | 6 | 7 |
| Sodium Laureth Sulfate | 6.5 | 8.5 | 9.5 | 8.5 | 9.0 | 8.75 | 7.0 |
| Cocamidopropyl Betaine | 3.0 | 3.0 | | 3.2 | 3.5 | 2.9 | 2.8 |
| Sodium Myreth Sulfate | 3.0 | | | | | | 2.5 |
| Disodium Cocoyl Glutamate | | | | 0.5 | | | |
| Decyl Glucoside | | 1.0 | | | | | 1.0 |
| Coco Glucoside | | | 1.0 | | | | |
| Coco Betaine | | | 2.0 | | | | |
| AMA-X Polymer | 1.44 | 1.30 | 1.28 | 1.28 | 1.30 | 1.44 | 1.40 |
| PEG-7 Glyceryl Cocoate | 1.0 | 1.0 | 1.5 | 1.0 | 1.75 | 2.0 | 1.0 |
| PEG-40 Hydrogenated Castor Oil | 0.8 | 0.6 | 0.6 | 0.6 | 0.8 | 0.6 | 0.7 |
| Benzophenone-4 | | 0.05 | | 0.02 | 0.05 | | |
| Glycerol | | | | | 1.0 | | |
| Sodium Benzoate | 0.5 | 0.45 | 0.4 | 0.45 | 0.45 | 0.4 | 0.5 |
| Sodium Salicylate | | | 0.2 | | 0.1 | 0.15 | |
| Helianthus Annuus Seed Oil | | 0.1 | | | 0.1 | | 0.01 |
| Cosmospheres ®* | 0.05 | 0.08 | | 0.15 | 0.08 | | |
| Unispheres ®** | | | 0.1 | | | 0.2 | 0.15 |
| Polyethylene particle | 0.1 | | | 0.2 | | | |
| CI 42090 | | | 0.0001 | | | 0.002 | |
| CI 10316 | | | 0.002 | | | | |
| Citric Acid | q.s. | q.s. | q.s. | q.s. | q.s. | q.s. | q.s. |
| Sodium Hydroxide | q.s. | q.s. | q.s. | q.s. | q.s. | q.s. | q.s. |
| Perfume | 1.0 | 0.9 | 1.0 | 0.8 | 0.85 | 1.0 | 1.0 |
| Aqua | ad 100 | ad 100 | ad 100 | ad 100 | ad 100 | ad 100 | ad 100 |
| Example No. | 8 | 9 | 10 | 11 | 12 | 13 | 14 |
| Sodium Laureth Sulfate | 8.0 | 8.5 | 8.5 | 7.5 | 9.0 | 8.5 | 9.5 |
| Cocamidopropyl Betaine | 3.0 | 3.0 | | 3.0 | 3.0 | 2.9 | |
| Sodium Myreth Sulfate | | | | 2.0 | | | |
| Disodium Cocoyl Glutamate | 1.0 | | 0.5 | | | | |
| Decyl Glucoside | | | 1.0 | | | 0.5 | |
| Coco Glucoside | | 1.5 | | | 0.8 | 0.8 | 1.0 |
| Coco Betaine | | | 2.0 | | | | 2.0 |
| AMA-X Polymer | 1.44 | 1.28 | 1.28 | 1.32 | 1.40 | 1.60 | 1.28 |
| PEG-7 Glyceryl Cocoate | 1.2 | 1.0 | 1.0 | 1.0 | | 1.1 | 1.0 |
| PEG-40 Hydrogenated Castor Oil | 0.65 | 0.6 | 0.7 | 0.6 | 0.8 | 0.65 | 0.6 |
| Benzophenone-4 | | 0.05 | | 0.05 | 0.06 | 0.05 | 0.03 |
| Glycerol | | | 0.5 | | | | |
| Sodium Benzoate | 0.4 | 0.45 | 0.5 | 0.45 | 0.35 | 0.40 | 0.45 |
| Sodium Salicylate | 0.1 | | | | 0.40 | 0.10 | |
| Helianthus Annuus Seed Oil | 0.01 | | | 0.1 | | | 0.1 |
| PEG-200 Hydrogenated Glyceryl Palmate | | 0.8 | | | 0.2 | | |
| Cosmospheres ®* | 0.2 | | | 0.15 | | | |
| Unispheres ®** | | 0.13 | | | | 0.11 | 0.08 |
| Polyethylene particle | | | 0.3 | | 0.09 | 0.05 | |
| CI 42090 | | | | | | 0.0001 | |
| CI 15985 | | 0.0005 | | | | | |
| Citric Acid | q.s. | q.s. | q.s. | q.s. | q.s. | q.s. | q.s. |
| Sodium Hydroxide | q.s. | q.s. | q.s. | q.s. | q.s. | q.s. | q.s. |
| Perfume | 1.0 | 0.8 | 0.9 | 1.0 | 1.1 | 0.85 | 1.0 |
| Aqua | ad 100 | ad 100 | ad 100 | ad 100 | ad 100 | ad 100 | ad 100 |

| Shower gels (the quantities are active contents) | | | | | | |
|---|---|---|---|---|---|---|
| Example No. | 15 | 16 | 17 | 18 | 19 | 20 |
| Sodium Laureth Sulfate | 9.0 | 9.0 | 8.5 | 7.0 | 6.5 | 7.5 |
| Cocamidopropyl Betaine | 3.0 | 3.0 | 3.1 | 3.0 | 3.2 | 3.0 |
| Sodium Myreth Sulfate | | | | 2.0 | 3.0 | |
| Disodium Cocoyl Glutamate | | | 0.5 | | | 1.0 |
| Decyl Glucoside | | 1.0 | 0.2 | | | 0.3 |
| Coco Glucoside | | | 0.3 | 0.5 | 0.6 | 0.4 |
| AMA-X Polymer | 1.28 | 1.44 | 1.45 | 1.40 | 1.35 | 1.44 |
| PEG-7 Glyceryl Cocoate | 1.0 | 1.5 | 1.2 | 1.0 | 1.1 | |
| PEG-40 Hydrogenated Castor Oil | 0.6 | 0.6 | 0.8 | 0.7 | 0.65 | 0.6 |
| Benzophenone-4 | 0.05 | 0.05 | | 0.04 | | |
| Glycerol | | | | | 1.0 | |
| Sodium Benzoate | 0.45 | 0.45 | 0.40 | 0.35 | 0.50 | 0.4 |
| Sodium Salicylate | | | 0.10 | 0.15 | | 0.1 |
| Helianthus Annuus Seed Oil | 0.1 | | | 0.01 | | |
| Cosmospheres ®* | | 0.08 | | | 0.07 | |
| Unispheres ®** | 0.1 | | 0.15 | | | 0.13 |
| Polyethylene particle | | | | 0.1 | | |
| CI 10316 | | | 0.002 | | | |
| CI 16035 | | | | | 0.0004 | |
| Citric Acid | q.s. | q.s. | q.s. | q.s. | q.s. | q.s. |
| Sodium Hydroxide | q.s. | q.s. | q.s. | q.s. | q.s. | q.s. |
| Perfume | 1.0 | 0.9 | 0.85 | 1.0 | 1.0 | 1.3 |
| Aqua | ad 100 | ad 100 | ad 100 | ad 100 | ad 100 | ad 100 |
| Example No. | 21 | 22 | 23 | 24 | 25 | 26 |
| Sodium Laureth Sulfate | 9.0 | 9.0 | 8.5 | 7.0 | 6.5 | 7.5 |
| Cocamidopropyl Betaine | 3.0 | 3.0 | 3.1 | 3.0 | 3.2 | 3.0 |
| Sodium Myreth Sulfate | | | | 2.0 | 3.0 | |
| Disodium Cocoyl Glutamate | | | 0.5 | | | 1.0 |
| Decyl Glucoside | | 1.0 | 0.2 | | | 0.3 |
| Coco Glucoside | | | 0.3 | 0.5 | 0.6 | 0.4 |
| AMA-X Polymer | 1.28 | 1.44 | 1.45 | 1.40 | 1.35 | 1.44 |
| PEG-7 Glyceryl Cocoate | 1.0 | 1.5 | 1.2 | 1.0 | 1.1 | |
| PEG-40 Hydrogenated Castor Oil | 0.6 | 0.6 | 0.8 | 0.7 | 0.65 | 0.6 |
| Benzophenone-4 | 0.05 | 0.05 | | 0.04 | | |
| Glycerol | | | | | 1.0 | |
| Sodium Benzoate | 0.45 | 0.45 | 0.40 | 0.35 | 0.50 | 0.4 |
| Sodium Salicylate | | | 0.10 | 0.15 | | 0.1 |
| Glycine Soja | 0.1 | | | 0.01 | 0.1 | 0.05 |
| Mineral Oil | | 0.05 | | | | 0.05 |
| Ricinus Communis | | | 0.08 | | 0.01 | |
| Cosmospheres ®* | | 0.08 | | | 0.07 | |
| Unispheres ®** | 0.1 | | 0.15 | | | 0.13 |
| Polyethylene particle | | | | 0.1 | | |
| CI 10316 | | | 0.002 | | | |
| CI 16035 | | | | | 0.0004 | |
| Citric Acid | q.s. | q.s. | q.s. | q.s. | q.s. | q.s. |
| Sodium Hydroxide | q.s. | q.s. | q.s. | q.s. | q.s. | q.s. |
| Perfume | 1.0 | 0.9 | 0.85 | 1.0 | 1.0 | 1.3 |
| Aqua | ad 100 | ad 100 | ad 100 | ad 100 | ad 100 | ad 100 |
| Example No. | 27 | 28 | 29 | 30 | 31 | 32 |
| Sodium Laureth Sulfate | 9.0 | 9.0 | 8.5 | 7.0 | 6.5 | 7.5 |
| Cocamidopropyl Betaine | 3.0 | 3.0 | 3.1 | 3.0 | 3.2 | 3.0 |
| Sodium Myreth Sulfate | | | | 2.0 | 3.0 | |
| Disodium Cocoyl Glutamate | | | 0.5 | | | 1.0 |
| Decyl Glucoside | | 1.0 | 0.2 | | | 0.3 |
| Coco Glucoside | | | 0.3 | 0.5 | 0.6 | 0.4 |
| AMA-X Polymer | 1.28 | 1.44 | 1.45 | 1.40 | 1.35 | 1.44 |
| PEG-7 Glyceryl Cocoate | 1.0 | 1.5 | 1.2 | 1.0 | 1.1 | |
| PEG-40 Hydrogenated Castor Oil | 0.6 | 0.6 | 0.8 | 0.7 | 0.65 | 0.6 |
| Benzophenone-4 | 0.05 | 0.05 | | 0.04 | | |
| Glycerol | | | | | 1.0 | |
| Sodium Benzoate | 0.45 | 0.45 | 0.40 | 0.35 | 0.50 | 0.4 |
| Sodium Salicylate | | | 0.10 | 0.15 | | 0.1 |
| Glycine Soja | 0.1 | | | 0.01 | 0.1 | 0.05 |
| Mineral Oil | | 0.05 | | | | 0.05 |
| Ricinus Communis | | | 0.08 | | 0.01 | |
| CI 10316 | | | 0.002 | | | |
| CI 16035 | | | | | 0.0004 | |

-continued

| Shower gels (the quantities are active contents) | | | | | | |
|---|---|---|---|---|---|---|
| Citric Acid | q.s. | q.s. | q.s. | q.s. | q.s. | q.s. |
| Sodium Hydroxide | q.s. | q.s. | q.s. | q.s. | q.s. | q.s. |
| Perfume | 1.0 | 0.9 | 0.85 | 1.0 | 1.0 | 1.3 |
| Aqua | ad 100 | ad 100 | ad 100 | ad 100 | ad 100 | ad 100 |

| Shampoos (the quantities are active contents): | | | | | | |
|---|---|---|---|---|---|---|
| Example No. | 1 | 2 | 3 | 4 | 5 | 6 |
| Sodium Laureth Sulfate | 8.5 | 11.0 | 9.5 | 7.5 | 10.0 | 11.7 |
| Cocamidopropyl Betaine | 3.0 | 3.2 | 3.8 | 2.2 | 3.1 | 4 |
| Cocamide DEA | | | | 2.0 | 1.0 | |
| Decyl Glucoside | | 1.0 | 0.2 | | | 0.3 |
| AMA-X Polymer | 1.6 | 1.2 | 1.3 | 1.8 | 1.35 | 1.12 |
| PEG-40 Hydrogenated Castor Oil | 0.6 | 0.6 | 0.8 | 0.7 | 0.65 | 0.6 |
| Benzophenone-4 | 0.05 | 0.05 | 0.05 | 0.04 | 0.05 | 0.05 |
| Polyquaternium-10 | 0.3 | | | | 0.3 | |
| Guar Hydroxypropyltrimonium Chloride | | 0.15 | | | 0.1 | 0.2 |
| Sodium Benzoate | 0.45 | 0.6 | 0.40 | 0.35 | 0.50 | 0.4 |
| Sodium Salicylate | | | 0.10 | 0.15 | | 0.1 |
| PEG-3 Distearate | | | | 1.0 | | 1.5 |
| Styrene/Acrylates Copolymer | 0.5 | | | | | |
| Zinc Pyrithione | | 0.1 | | | 0.2 | |
| Sodium Chloride | | 0.8 | | | | 1.0 |
| Citric Acid | q.s. | q.s. | q.s. | q.s. | q.s. | q.s. |
| Sodium Hydroxide | q.s. | q.s. | q.s. | q.s. | q.s. | q.s. |
| Perfume | 1.0 | 0.9 | 0.85 | 1.0 | 1.0 | 1.3 |
| Aqua | ad 100 | ad 100 | ad 100 | ad 100 | ad 100 | ad 100 |

| Example No. | 7 | 8 | 9 | 10 | 11 |
|---|---|---|---|---|---|
| Sodium Laureth Sulfate | 7 | 10 | 12 | 0.11 | 0.12 |
| Cocamidopropyl Betaine | 1.3 | 2.5 | 4 | | |
| Cocamide DEA | 2 | 1.5 | 1 | | |
| Lauryl Glucoside | | | | 4.3 | 4.8 |
| Sodium Myreth Sulfate | | | | 2.8 | 3.2 |
| PEG-80 Sorbitan Laurate | | | | 2.6 | 2.3 |
| Disodium PEG-5 Lauryl citrate Sulfosuccinate | | | | 2.1 | 2.3 |
| AMA-X Polymer | 1.6 | 1.2 | 1.3 | 2.0 | 1.9 |
| PEG-7 Glyceryl Cocoate | 1.0 | | 1.2 | | 0.5 |
| PEG-40 Hydrogenated Castor Oil | 0.6 | 0.6 | 0.8 | 0.7 | 0.65 |
| Benzophenone-4 | 0.05 | 0.05 | 0.05 | 0.04 | 0.05 |
| Dimethicone | 0.7 | 2.2 | | | |
| Polyquaternium-10 | | | 0.2 | | 0.3 |
| Guar hydroxyproypltrimonium Chloride | 0.3 | | | 0.1 | |
| Sodium Benzoate | 0.2 | 0.45 | 0.40 | 0.35 | 0.4 |
| Sodium Salicylate | 0.2 | | 0.10 | 0.15 | |
| PEG-200 Hydrogenated Glyceryl Palmate | | | | 2 | 1 |
| PEG-90 Glyceryl Isostearate + Laureth-2 | | | | | 1 |
| PEG-3 Distearate | 1.5 | | | | |
| Styrene/Acrylates Copolymer | | | | | 0.5 |
| Climbazole | 0.4 | | | | |
| Piroctone Olamine | | 0.45 | | | |
| Zinc Pyrithione | | | | 0.2 | |
| Sodium Chloride | | 1.0 | | | |
| Citric Acid | q.s. | q.s. | q.s. | q.s. | q.s. |
| Sodium Hydroxide | q.s. | q.s. | q.s. | q.s. | q.s. |
| Perfume | 1.0 | 0.9 | 0.85 | 1.0 | 1.0 |
| Aqua | ad 100 | ad 100 | ad 100 | ad 100 | ad 100 |

| Facial cleanser (the quantities are active contents): | | | | | | | |
|---|---|---|---|---|---|---|---|
| Example No. | 1 | 2 | 3 | 4 | 5 | 5 | 6 |
| Sodium Laureth Sulfate | 2.0 | 4 | | | | 1.5 | |
| Cocamidopropyl Betaine | | | 3.8 | 6.2 | 4.3 | | |
| Sodium Cocoamphoacetate | | | | | | | 6.0 |
| Sodium Myreth Sulfate | | | 3.1 | 3.5 | 2.6 | | 3.0 |
| Coco Glucoside | 2.5 | 3.8 | | | | | |
| Lauryl Glucoside | | | 1.0 | | 0.9 | | 2.5 |
| Decyl Glucoside | | | | 2.0 | | 0.26 | |
| Sodium Methyl Cocoyl Taurate | | | | | | 0.45 | |
| AMA-X Polymer | 1.1 | 1.3 | 1.2 | 1.75 | 1.4 | 1.9 | 1.5 |
| PEG-40 Hydrogenated Castor Oil | 0.6 | 0.5 | 0.5 | 0.4 | 0.5 | | 0.8 |
| PEG-7 Glyceryl Cocoate | | | | | | 0.5 | |
| Benzophenone-4 | 0.05 | 0.05 | 0.05 | | | 0.05 | |
| Polyquaternium-10 | 0.2 | | 0.1 | 0.15 | | | 0.2 |
| Glycerol | | | 1.9 | | 1 | 1.5 | |
| Sodium Benzoate | 0.45 | 0.5 | 0.45 | 0.45 | 0.45 | 0.45 | 0.45 |
| Sodium Salicylate | | | 0.40 | 0.40 | 0.40 | 0.35 | 0.4 |
| PEG-200 Hydrogenated Glyceryl Palmate | | | 0.5 | | 0.7 | | 0.5 |
| PEG-90 Glyceryl Isostearate + Laureth 2 | | | | 1 | | | |
| Panthenol | | | 0.1 | | 0.1 | | |
| Vitamin E Acetate | | 0.1 | | | 0.1 | | |
| Cosmospheres ®* | | | | | 0.3 | | |
| Unispheres ®** | 0.1 | | | | | | 0.2 |
| Polyethylene particle | | 0.2 | | | | | |
| Citric Acid | q.s. | q.s. | q.s. | q.s. | q.s. | q.s. | q.s. |
| Sodium Hydroxide | q.s. | q.s. | q.s. | q.s. | q.s. | q.s. | q.s. |
| Perfume | 0.5 | 0.5 | 0.4 | 0.3 | 0.4 | 0.1 | 0.5 |
| Aqua | ad 100 | ad 100 | ad 100 | ad 100 | ad 100 | ad 100 | ad 100 |

| Liquid soaps (the quantities are active contents): | | | |
|---|---|---|---|
| Example No. | 1 | 2 | 3 |
| Sodium Laureth Sulfate | 5 | 7 | 6.5 |
| Cocamidopropyl Betaine | 4.5 | 3.5 | 5.0 |
| AMA-X Polymer | 1.28 | 1.44 | 1.5 |
| PEG-7 Glyceryl Cocoate | 1.0 | | 0.5 |
| PEG-40 Hydrogenated Castor Oil | 0.3 | 0.5 | 0.2 |
| Glycerol | | 1 | |
| PEG-120 Methylglucose Dioleate | 0.3 | | |
| Sodium Benzoate | 0.45 | 0.45 | 0.40 |
| Sodium Salicylate | 0.40 | 0.40 | 0.10 |
| Helianthus Annuus Seed Oil | 0.1 | | |
| Almond oil | | 0.1 | |
| Styrene/Acrylates Copolymer | 0.4 | | |
| Glycol Distearate | | | 0.6 |
| Cosmospheres ®* | | 0.08 | |
| Unispheres ®** | 0.1 | | |
| CI 10316 | | | 0.002 |
| CI 16035 | 0.001 | | |
| Trisodium EDTA | 0.1 | | 0.1 |
| Citric Acid | q.s. | q.s. | q.s. |
| Sodium Hydroxide | q.s. | q.s. | q.s. |
| Perfume | 0.5 | 0.2 | 0.4 |
| Aqua | ad 100 | ad 100 | ad 100 |

*Cosmospheres ®: INCI designation: Lactose + Microcrystalline Cellulose + Helianthus Annuus Seed Oil + CI 77492 (optionally also with active ingredients and dyes other than Helianthus Annus Seed and CI 77492) as solid particles.
**Unispheres ®: INCI designation: Lactose + Cellulose + CI 77007 + Hydroxypropyl Methylcellulose + Tocopheryl Acetate (optionally also with active ingredients and dyes other than Tocopheryl Acetate and CI 77007) as solid particles.

Comparative Test to Determine Mildness:

| Inventive preparation: | [g] | |
|---|---|---|
| Polymer phase | | |
| Aqua | 343.7 | present |
| AMA-X polymer (ca. 32%) | 49.4 | add |
| Surfactant phase | | |
| Sodium Laureth Sulfate (25%) | 360.0 | add to the polymer phase |
| Surfactant phase | | |
| [Cocamidopropyl Betaine + Glycerol] (34%) | 89.0 | add to the surfactant/polymer phase |
| NaOH phase | | |
| Sodium Hydroxide (45%) | ca. 3.0 | adjust pH of surfactant/polymer phase to 5.9! |
| Light filter phase | | |
| Aqua | 30.0 | Dissolve benzophenone-4 in water; add trisodium EDTA; add to the surfactant/polymer phase |
| Benzophenone-4 | 0.5 | |
| Trisodium EDTA (20%) | 10.0 | |

-continued

| Inventive preparation: | [g] | |
|---|---|---|
| Perfume phase | | |
| PEG-40 Hydrogenated Castor Oil | 6.0 | dissolve at 40° C. on magnetic stirrer; add to surfactant/polymer phase |
| Helianthus Annuus Seed Oil | 0.1 | |
| PEG-7 Glyceryl Cocoate | 10.0 | |
| Perfume | 13.0 | |
| Preservative phase: | | |
| Aqua | 30.0 | dissolve sodium benzoate in water; add to surfactant/polymer phase |
| Sodium Benzoate | 4.5 | |
| Citric acid | | |
| Aqua | 4.5 | adjust pH to 4.8-5.2 |
| Citric Acid | 0.5 | |
| Beads | | |
| Lactose + Microcrystalline Cellulose + Helianthus Annuus Seed Oil + CI77492 | 0.8 | add to mixture |
| Total batch amount | 1000.0 | |

A standard RBC test (WAS) to determine the mildness was conducted with the preparation according to the invention thus obtained and a commercial product (Balea Dusche & Ölperlen Queen of the Night).

| Test sample | $H^{50}$ [µl/ml] | DI | L/D |
|---|---|---|---|
| Balea Dusche&Ölperlen Queen of the Night | 16.6 | 50.3 | 0.33 |
| Inventive preparation | 16.5 | 34.0 | 0.48 |

The L/D values, which provide evidence for the mildness of a preparation, are higher for the preparation according to the invention than for the commercial product. This shows that the mildness of the inventive preparation is better.

What is claimed is:

1. An aqueous cosmetic preparation, wherein the preparation is present as a shower gel and comprises one or more surfactants and from 0.1% to 1.6% by weight of one or more AMA-X polymers, based on an active content and a total weight of the preparation.

2. The preparation of claim 1, wherein the preparation comprises particles, droplets and/or bubbles stably distributed therein.

3. The preparation of claim 1, wherein the preparation comprises from 1.0% to less than 10% by weight of one or more anionic surfactants, based on a total weight of the preparation.

4. The preparation of claim 1, wherein the preparation further comprises from 0.1% to 3.0% by weight of one or more salts, based on a total weight of the preparation.

5. The preparation of claim 1, wherein the preparation has a pH value of from 4.0 to <6.4.

6. The preparation of claim 1, wherein the preparation exhibits a mildness, measured as a ratio L/D in an RBC assay, of ≤0.4.

* * * * *